United States Patent [19]

Kuder

[11] 4,404,070

[45] Sep. 13, 1983

[54] ELECTROCHEMICAL PRODUCTION OF 2,6-DIAMINOBENZOBISTHIAZOLE

[75] Inventor: James E. Kuder, Fanwood, N.J.

[73] Assignee: Celanese Corporation, New York, N.Y.

[21] Appl. No.: 401,437

[22] Filed: Jul. 23, 1982

[51] Int. Cl.$^3$ ............................................... C25B 3/10
[52] U.S. Cl. .......................................... 204/72; 204/78
[58] Field of Search ..................................... 204/72, 78

[56] References Cited

U.S. PATENT DOCUMENTS 3,025,303 3/1962 Ifversen et al. .................. 204/78 X

OTHER PUBLICATIONS

Melnikov et al., Chemical Abstracts, vol. 29, Col. 934 (1945).

Encyclopedia of Electrochemistry by Hampel, pub. by Reinhold, New York (1964).

*Primary Examiner*—F. Edmundson
*Attorney, Agent, or Firm*—Depaoli & O'Brien

[57] ABSTRACT

This invention provides an electrochemical process for the production of 2,6-diaminobenzobisthiazole by the interaction of p-phenylenediamine with a thiocyanate salt in an acidic aqueous medium under electrolysis conditions.

8 Claims, No Drawings

ELECTROCHEMICAL PRODUCTION OF 2,6-DIAMINOBENZOBISTHIAZOLE

BACKGROUND OF THE INVENTION

There are several methods described in the chemical literature for the synthesis of diaminobenzobisthiazoles and related compounds. Various disadvantages are associated with these procedures.

French Pat. No. 1,224,183 and J. Org. Chem., 33, 2132 (1968) disclose the reaction of p-phenylenediamine, ammonium thiocyanate and bromine in acetic acid to yield diaminobenzobisthiazole compounds. The compound 2,6-diaminobenzobisthiazole is produced by means of the following illustrated reaction series:

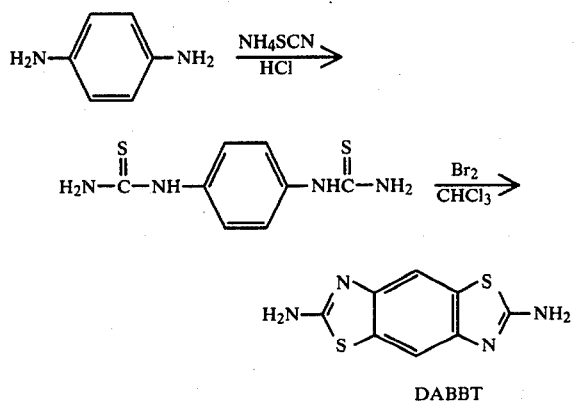

DABBT

Hydrolysis of 2,6-diaminobenzobisthiazole followed by acidification affords a salt of diaminobenzenedithiol (DABDT), which is useful as a comonomer in the preparation of polybenzthiazole (PBT):

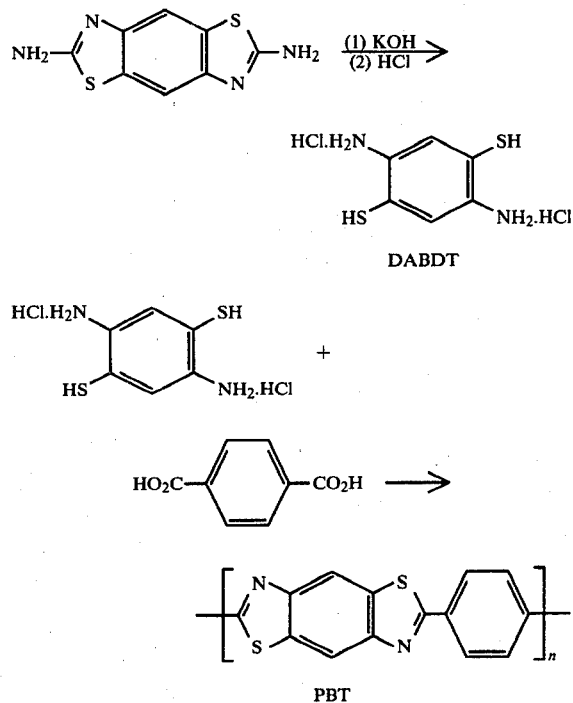

PBT

Among the disadvantages of prior art methods for synthesizing diaminobenzobisthiazole compounds are the use of corrosive and toxic reactants such as bromine and chloroform. Any prospective large scale process for diaminobenzobisthiazole production would endeavor to avoid the use of such noxious chemicals.

An alternative route of potential interest is the synthesis of amino-substituted aromatic compounds via an electrochemical reaction mechanism.

Chemical Abstracts, Vol. 39, Col. 934 (1945) discloses a procedure for producing 2-amino-6-methylbenzothiazole from p-toluidine and ammonium thiocyanate in $HCl/C_2H_5OH$ under electrolysis conditions.

Encyclopedia Of Electrochemistry (1964), pages 532–536, discloses the reaction of electrochemically-generated thiocyanogen with organic compounds.

There remains a need for a safe and efficient process for providing useful heterocyclic compounds such as diaminobenzobisthiazoles.

Accordingly, it is an object of this invention to provide a process for the production of diaminobenzobisthiazole compounds which does not involve the use of noxious reagents.

It is another object of this invention to provide an electrochemical process for the production of 2,6-diaminobenzobisthiazole.

Other objects and advantages of the present invention shall become apparent from the accompanying description and examples.

DESCRIPTION OF THE INVENTION

One or more objects of the present invention are accomplished by the provision of an electrochemical process for the production of 2,6-diaminobenzobisthiazole which comprises subjecting an acidic aqueous medium containing p-phenylenediamine and a thiocyanate salt to electrolysis conditions, and recovering 2,6-diaminobenzobisthiazole as a precipitated product.

Suitable thiocyanate salts which may be employed include ammonium thiocyanate and alkali metal salts such as sodium thiocyanate and potassium thiocyanate.

It is essential that the electrolysis is conducted under mild temperature conditions, e.g., at a temperature between about $-20°$ C. and $30°$ C. The efficiency of the electrochemical process decreases as the reaction medium temperature increases. It appears that higher temperatures adversely affect the availability of reactive thiocyanate species.

The required acidity of the aqueous electrolysis medium is provided by a mineral acid such as hydrochloric acid, phosphoric acid, sulfuric acid, and the like, or by a water-miscible organic acid such as methanesulfonic acid, acetic acid, trichloroacetic acid, and the like.

It is advantageous for purposes of the invention process to include a non-reactive water-miscible organic solvent in the aqueous electrolysis medium. Illustrative of suitable water-miscible solvents are alkanols such as methanol, butanol and ethylene glycol; ethers such as tetrahydrofuran and 1,2-dimethoxyethane; ketones such as acetone and methyl ethyl ketone; esters such as methyl acetate and ethyl acetate; organic acids such as acetic acid and oxalic acid; and the like. The presence of a water-miscible organic solvent improves the solubility properties of the aqueous medium and serves to enhance the reaction rate and efficiency of the p-phenylenediamine and thiocyanate salt interaction, and permits low temperature cooling of the aqueous medium without solidification.

Depending on the various parameters being employed in the invention electrochemical process, the 2,6-diaminobenzobisthiazine product may precipitate out of the electrolysis medium in the form of acid salt. Preferably, the electrolysis conditions are controlled so as to maintain the said acid salt in solution during the course of the electrolysis. Precipitation of the product can be effected either by concentration and/or cooling of the reaction medium, and/or by the addition of an alkaline reagent to adjust the pH of the electrolysis medium into the range between about 7–12. An alkaline reagent such as ammonium hydroxide or sodium carbonate is suitable for this purpose. Under alkaline conditions, the free amine product is obtained instead of the acid salt.

As illustrated in the Examples, either an undivided or divided electrolytic cell may be employed for the invention electrochemical process. In the case of a divided cell, it is required that there are p-phenylenediamine and thiocyanate salt present in the anodic compartment.

One proposed mechanism for the electrochemistry involves anodic oxidation of thiocyanate to thiocyanogen, and the ensuing interaction of the electrochemically-generated thiocyanogen with p-phenylenediamine to form a 1,4-diamino-2,5-dithiocyanobenzene intermediate:

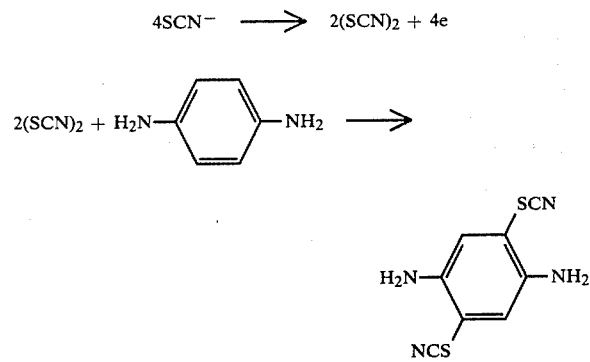

Another proposed mechanism involves the partial oxidation of p-phenylenediamine, then interaction of this species with thiocyanate ion, followed by further oxidation to the 1,4-diamino-2,5-dithiocyanobenzene intermediate:

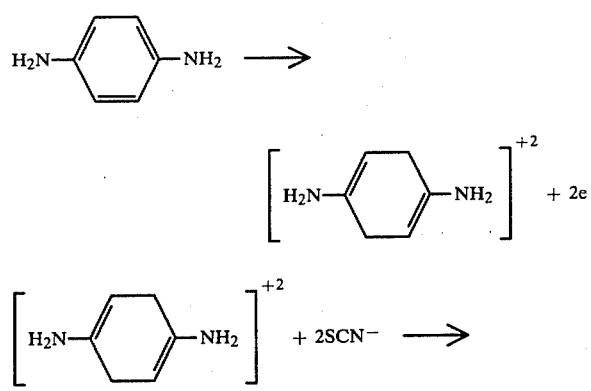

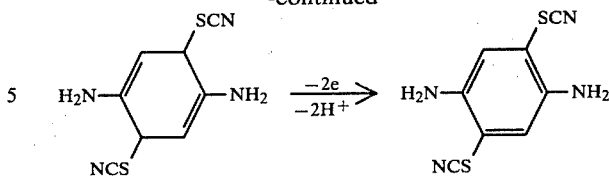

The resultant 1,4-diamino-2,5-dithiocyanobenzene intermediate undergoes spontaneous cyclization to form the desired 2,6-diaminobenzobisthiazole product of the electrochemical process.

As it is apparent, the invention process also is adapted to produce a non-linear diaminobenzobisthiazole such as 2,6-diaminobenzo-[1,2-d: 5,4-d']bisthiazole:

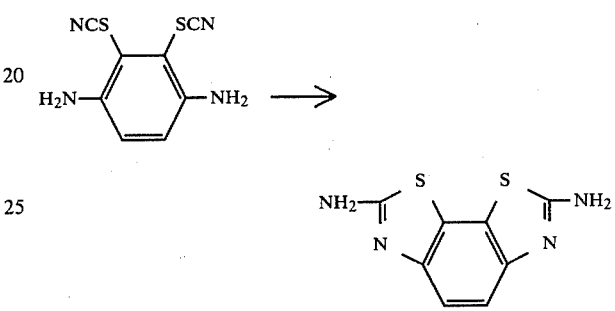

The following Examples are further illustrative of the present invention. The catalysts and other specific ingredients and processing parameters are presented as being typical, and various modifications can be derived in view of the foregoing disclosure within the scope of the invention.

EXAMPLE I

This Example illustrates the application of the invention electrochemical process for the production of 2,6-diaminobenzobisthiazole (DABBT) in a one compartment electrolysis cell.

Into a water-jacketed undivided cell equipped with one-fourth inch spectroscopic carbon rods as anode and cathode, saturated calomel electrode (SCE) as reference electrode and magnetic stirring bar were charged ammonium thiocyanate (4.51 g, 0.059 mole, Fisher ACS grade), p-phenylenediamine (1.08 g, 0.01 mole, Fisher certified), and 2 ml of concentrated hydrochloric acid dissolved in 40 ml of 1:1 ethanol-water. The temperature of the solution was maintained at 15°–16° C. by means of water circulating through the jacket of the cell, and the solution was continuously stirred.

A controlled potential of $+1.2$V vs SCE was applied to the working electrode by means of an Eco Model 549 potentiostat. The current at the beginning was 190 ma (current density 14 ma/cm$^2$) and after the passage of 0.90 amp-hour had decreased to 25 ma (2 ma/cm$^2$) at which point the electrolysis was discontinued. The amount of electricity theoretically required for complete reaction was calculated as (0.01 mole) (4-equivalents/mole) (26.8 amp-hours/equivalent) or 1.07 amp-hours (via the thiocyanogen mechanism).

The electrolysis solution was filtered through fluted filter paper and 0.039 g of dark-brown solid collected. The filtrate was made basic (pH 10) with concentrated aqueous ammonia. The blue precipitate which formed upon addition of ammonia was collected on fluted filter paper and after drying weighed 0.09 g. Both solids had melting points greater than 300° C.

Examination of both samples by infrared spectroscopy showed the presence of the desired product of the thiocyanation reaction in addition to unreacted p-phenylenediamine (PPDA). Mass spectral examination showed PPDA (m/e 108), DABBT (m/e 222) and the monothiocyano derivative of PPDA (m/e 165). The n.m.r. spectrum showed signals consistent with para and ortho-DABBT plus unreacted PPDA. On the basis of signal intensity the DABBT content was 10–20 mole percent.

EXAMPLE II

This Example illustrates the application of the invention electrochemical process for the production of 2,6-diaminobenzobisthiazole in a two compartment electrolysis cell.

A solution containing 18.24 g (0.24 mole) of $NH_4SCN$ in 150 ml of ethanol-water (2:1) was prepared, and 75 ml of the solution was placed in each compartment of a divided H-cell. Two milliliters of 36% aqueous HCl was added to each compartment, and the cell was cooled to $-5°$ C. p-Phenylenediamine (3.24 g, 0.03 mole, recrystallized from water) was added to the anode compartment which was equipped with a magnetic stirring bar. Carbon rods served both as anode and cathode. The solution was subjected to controlled potential electrolysis at 1.4V vs SCE until 1.1 amp-hours of electricity had been passed.

A brown solid (0.048 g) which precipitated from the solution on standing overnight was collected by filtration. After adjusting the pH to 10 with ammonia, two additional crops of solid (0.020 g and 0.199 g) were collected. All three solids had melting points greater than 300° C. Mass spectral examination of these solids indicated the presence of p-phenylenediamine and DABBT, the relative amount of DABBT increasing from the first solid to the last solid collected.

What is claimed is:

1. An electrochemical process for the production of 2,6-diaminobenzobisthiazole which comprises subjecting an acidic aqueous medium containing p-phenylenediamine and a thiocyanate salt to electrolysis conditions, adjusting the pH of the acidic medium to at least about 7 with an alkaline reagent, and recovering 2,6-diaminobenzobisthiazole as a precipitated product.

2. A process in accordance with claim 1 wherein the thiocyanate salt is alkali metal thiocyanate.

3. A process in accordance with claim 1 wherein the thiocyanate salt is ammonium thiocyanate.

4. A process in accordance with claim 1 wherein the electrolysis reaction is conducted at a temperature between about $-20°$ C. and 30° C.

5. A process in accordance with claim 1 wherein the acidity of the aqueous medium is provided by mineral acid.

6. A process in accordance with claim 1 wherein the acidity of the aqueous medium is provided by a water-miscible carboxylic acid.

7. A process in accordance with claim 1 wherein the aqueous medium contains a water-miscible organic solvent.

8. A process in accordance with claim 1 wherein the aqueous medium contains a water-miscible alkanol.

* * * * *